(12) United States Patent
Machacek et al.

(10) Patent No.: US 6,450,328 B1
(45) Date of Patent: Sep. 17, 2002

(54) DENTAL EQUIPMENT AND MATERIAL STORAGE AND MULTI-POSITIONAL DISPLAY APPARATUS

(75) Inventors: Robert W. Machacek, Lombard; John R. Howard, Northwoods; Rich Nagel, West Chicago, all of IL (US)

(73) Assignee: Bisco, Inc., Schaumburg, IL (US)

( * ) Notice: Subject to any disclaimer, the term of this patent is extended or adjusted under 35 U.S.C. 154(b) by 0 days.

(21) Appl. No.: 09/570,706

(22) Filed: May 15, 2000

(51) Int. Cl.[7] ............................................. A61B 19/02
(52) U.S. Cl. .................. 206/63.5; 206/45.2; 206/45.24; 206/45.23
(58) Field of Search ........................... 206/45.2, 45.24, 206/45.23, 472, 473, 63.5, 379

(56) References Cited

U.S. PATENT DOCUMENTS

| | | | | |
|---|---|---|---|---|
| 468,224 A | * | 2/1892 | De Lancy Kennedy, Jr. | 206/473 |
| 1,445,593 A | * | 2/1923 | Iscowitz | 206/472 |
| 1,684,417 A | * | 9/1928 | Silberman | 206/63.5 |
| 1,879,029 A | * | 9/1932 | Baumgard | |
| 3,088,738 A | * | 5/1963 | Meyer | |
| 3,305,205 A | * | 2/1967 | Frankl | |
| 4,572,594 A | | 2/1986 | Schwartz | |
| 4,778,051 A | * | 10/1988 | Schaub et al. | 206/472 |
| 5,193,672 A | * | 3/1993 | Long | 206/45.2 |
| 5,720,464 A | | 2/1998 | Meinscher et al. | |
| 5,950,979 A | | 9/1999 | Mira | |
| 5,996,778 A | * | 12/1999 | Shih | 206/45.2 |
| 6,131,740 A | * | 10/2000 | Haung | 206/759 |

* cited by examiner

Primary Examiner—David T. Fidei
(74) Attorney, Agent, or Firm—Howrey, Simon, Arnold & White, LLP

(57) ABSTRACT

A storage and multi-positional display apparatus, particularly suited to dental equipment and materials, is disclosed. The apparatus includes a cover having individual rigid segments which are hinged together, with a storage tray secured to one of the segments. The apparatus can be transformed from a storage position wherein the segments are folded to form an enclosure surrounding the tray and protecting its contents, into one of many angled display positions wherein the tray is exposed. The angled positions mount the tray at an angular orientation best suited to the particular user performing a particular dental procedure, while the cover and tray provide for aseptic conditions and minimized cross-contamination of the dental equipment and material.

18 Claims, 3 Drawing Sheets

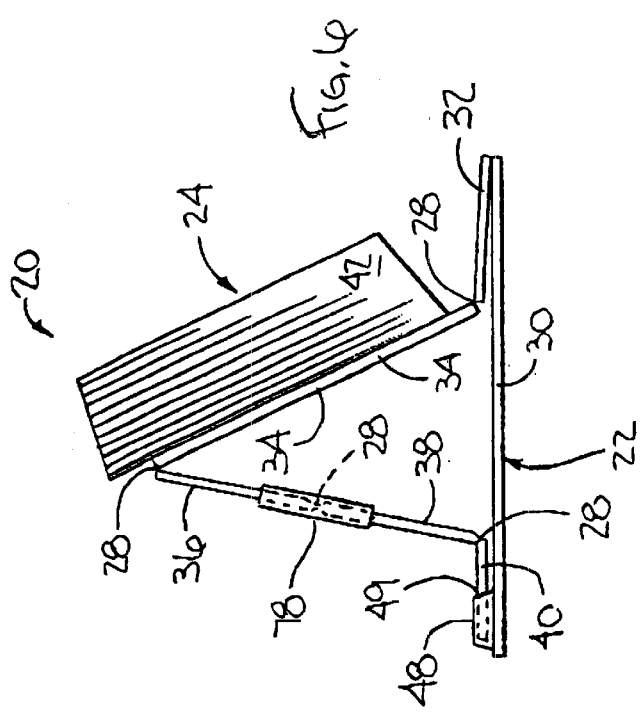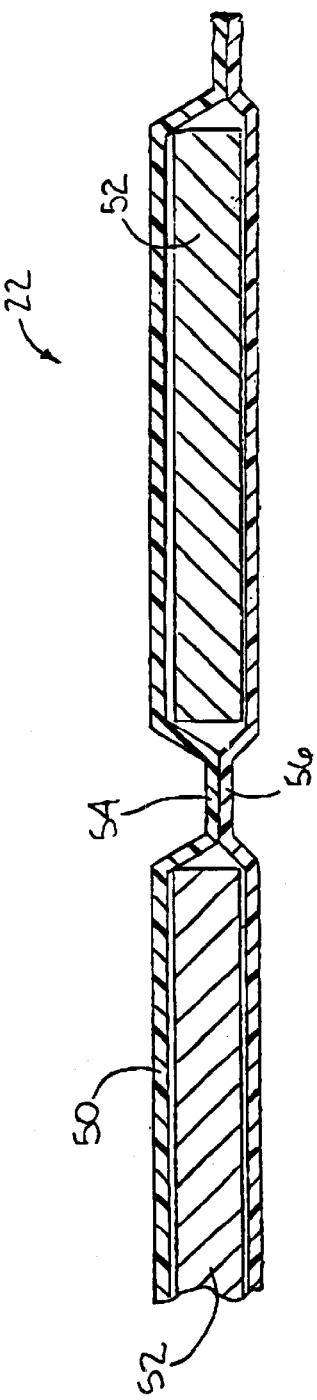

DENTAL EQUIPMENT AND MATERIAL STORAGE AND MULTI-POSITIONAL DISPLAY APPARATUS

BACKGROUND OF THE INVENTION

1. Field of the Invention

The invention generally relates to storage and display devices and, more particularly, the invention relates to devices adapted to store and display dental equipment and materials.

2. Description of the Related Technology

In many industries, it is desirable to store equipment and supplies related to a given task within a single package or toolbox for convenient access when the task needs to be performed. It is advantageous if the tools and equipment are provided in an organized fashion enabling the operator to quickly and repeatedly find the desired implement or supply. Various storage trays, holsters, tool belts, easels, and tool boxes have therefore been developed to service individual industries.

With particular reference to the field of dentistry, specific tools, chemicals, and composites are designed for particular dental maintenance and restoration procedures. When the procedures are to be performed, the tools and materials need to be accurately and readily grasped by the operator. Moreover, it is important that the equipment and supplies remain aseptic and not be subjected to cross-contamination in the process. When the procedure is completed, it is desirable to store the equipment and materials in an organized and centralized fashion to allow for quick retrieval for subsequent procedures.

SUMMARY OF THE INVENTION

According to the invention, a storage and multi-positional display apparatus is provided which includes a cover having a plurality of hinged segments, and a storage tray secured to one of the hinged segments. The storage tray is adapted to store dental equipment and materials and the cover is foldable from a storage position surrounding the storage tray, to at least one display position exposing the storage tray for ready access to the dental equipment. The cover may include a top, a first side, a bottom, a bottom extension, a second side, and an attachment flap allowing the cover to be foldable into multiple display positions, including vertical, horizontal, and angled with respect to the surface on which the apparatus is set.

These and other aspects and features of the invention will become more apparent from the following detailed description when taken in conjunction with the accompanying drawings and claims.

BRIEF DESCRIPTION OF THE DRAWINGS

FIG. 6 is a side view of an alternative embodiment of a dental equipment and material storage and multi-positional display apparatus according to the invention in a third display position; and FIG. 7 is a cross-sectional view through a portion of the cover.

Figure 1:
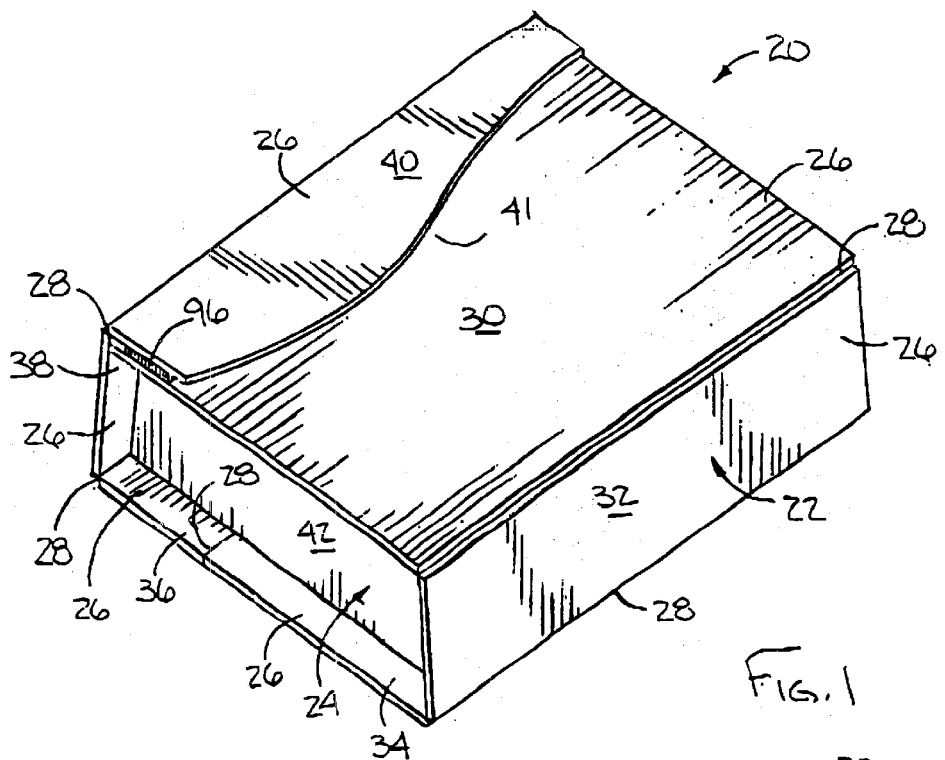
FIG. 1 is an isometric view of a dental equipment storage and multi-positional display apparatus according to the invention, shown in a closed position.

While the invention is susceptible of various modifications and alternative constructions, certain illustrative embodiments thereof have been shown in the drawings and are described below in detail. However, there is no intention to limit the invention to the specific forms disclosed, but on the contrary, the intention is to cover all modifications, alternative constructions, and equivalents falling within the spirit and scope of the invention as defined by the appended claims.

DETAILED DESCRIPTION OF THE PREFERRED EMBODIMENTS

Figure 2:
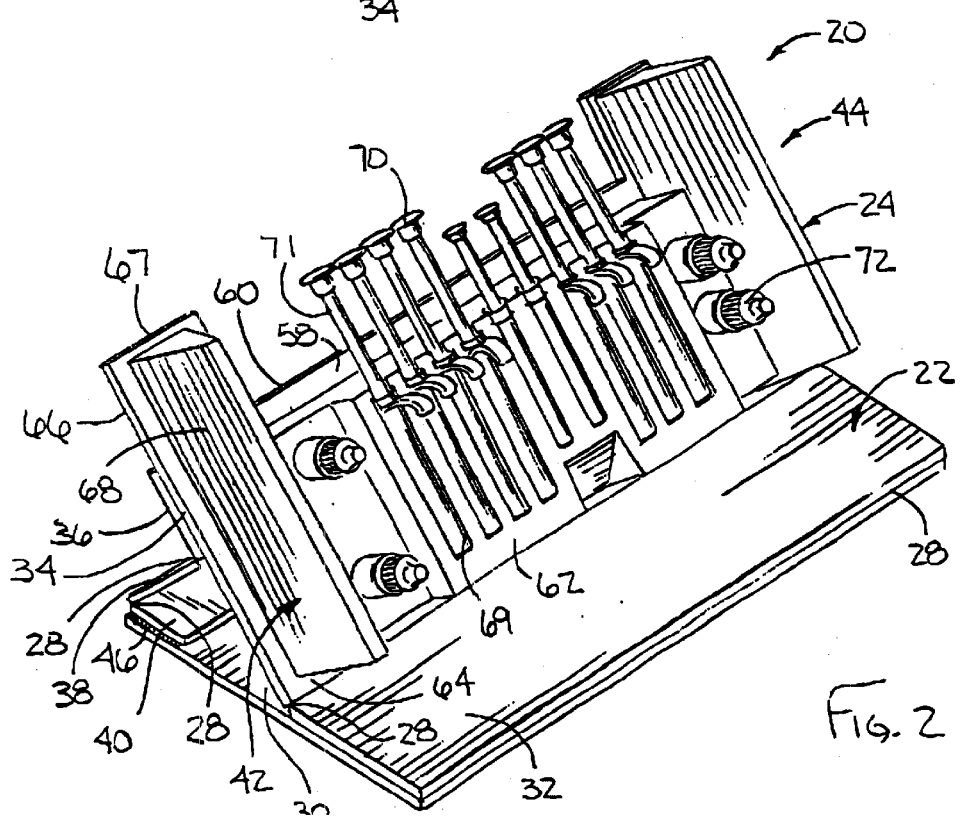
FIG. 2 is an isometric view of the dental equipment and material storage and multi-positional display apparatus of FIG. 1, shown in a display position.

Referring now to the drawings, and with specific reference to FIGS. 1 and 2, a dental equipment and material storage and multi-positional display apparatus according to the invention is generally depicted by reference numeral 20. The dental equipment and material storage and display apparatus 20 is depicted in FIG. 1 in a closed or storage position, and in FIG. 2 in a display or easel position at one of the various angles obtainable with the invention. In the stored position of FIG. 1, the contents of the apparatus 20 are completely enclosed, and protected from contamination during transportation or storage, whereas in the display position depicted in FIG. 2, the contents of the apparatus are readily displayed and easily selected and obtained by a user with minimized risk of cross-contamination. As used herein, the term "display" is therefore intended to not only convey that the contents of the apparatus are viewable, but that the contents can also be easily and quickly selected and accessed for use by the practitioner.

While the preferred embodiment of the invention is described with respect to dental equipment and material, it is to be understood that the invention can be employed with similar efficacy to other fields, including, but not limited to, art, construction, medicine, practically any type of presentation, and the like.

The storage and display apparatus 20 includes a cover 22 to which a storage tray 24 is secured. The cover 22 preferably includes a plurality of individual, substantially rigid, segments 26 connected by hinges 28. In the preferred embodiment, six segments 26 are provided including a top 30, a first side 32, a bottom 34, a bottom extension 36, a second side 38, and a connection flap 40.

Figure 3:
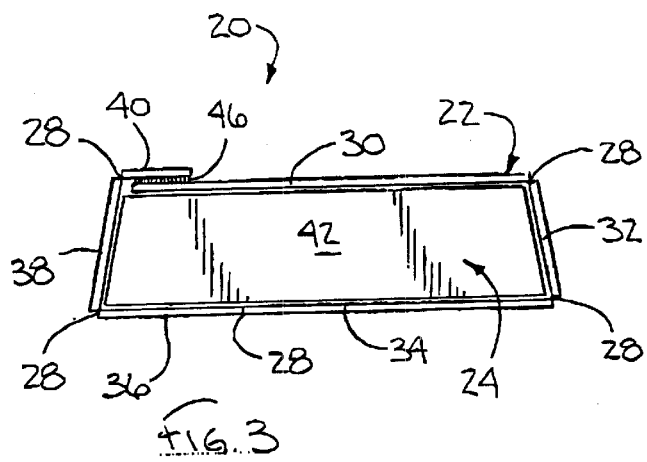
FIG. 3 is a side view of the storage and multi-positional display apparatus of FIG. 1, shown in a closed trapezoidal position.

The connection flap 40 is depicted having a curved edge 41, but it is to be understood that a variety of other shapes including, but not limited to, straight edges are possible. In the closed position, shown in FIGS. 1 and 3, the bottom 34 and the bottom extension 36 cooperate to form a single planar side of the apparatus 20, and the top 30 and connection flap 40 cooperate to form an opposed side of the apparatus 20. The first and second sides 32 and 38 form two additional sides of the apparatus 20, but are non-parallel to each other. As described in further detail below, the storage tray 24 includes first and second walls 42 and 44 which form the remaining sides of the six sided apparatus 20 to completely enclose the contents of the tray 24 when the apparatus 20 is closed. The resulting shape of the apparatus, as shown best in FIG. 3, is trapezoidal. This shape is of particular significance with respect to the alternative embodiment described later herein with respect to FIG. 6 in that it prevents sliding of top 30 relative to flap 40.

The connection flap 40 can be connected to the top 30 in a variety of ways, with the preferred embodiment using opposed strips 46 of hook and loop fasteners, a preferred embodiment using VELCRO® brand hook and loop fasteners, extending from the top 30 and connection flap 40. A number of other fastening devices could be employed. For example, in the alternative embodiment of FIG. 6, a band 48 of material extends from the top 30 and defines a longitudinal opening 49. The opening 49 is slightly smaller in cross-sectional area than the connection flap 40 such that the connection flap 40 frictionally engages the band 48 to secure the connection flap 40 to the top 30 when the apparatus 20 is in the closed position.

The cover 22 is preferably manufactured from a flexible material such as plastic, and as shown in FIG. 7 is provided in the form of a tube or sleeve 50. To provide each segment 26 with rigid support, individual rigid inserts 52 are positioned within the sleeve 50. First and second opposed surfaces 54 and 56 of the sleeve 50 are then heat sealed between adjacent inserts 52 to form the hinges 28 and completely seal each rigid insert 52 inside the sleeve 52. During the heat sealing process, a source of heat is directed against the surfaces 54 and 56 to melt the plastic sleeve 50 sufficiently to form a bond. The inserts 52 can be provided in the form of many rigid, or substantially rigid, materials including chipboard, cardboard, and the like.

As shown in FIG. 2, the storage tray 24 includes a substantially rectangular base 58 having a top 60, a front 62, a bottom 64, a back 66, and the first and second side walls 42 and 44. The side walls 42 and 44 are preferably formed from base portions 67 which extend beyond the base 58, and wedges 68 extending from the base portions 67. The wedges 68 are sized sufficiently long and high to completely close two sides of the apparatus 20. The tray 24 further includes a plurality of compartments 69 sized and shaped to frictionally receive a variety of instruments and materials, with the preferred embodiment including syringes 70 for dispensing dental materials, as well as bottles or vials 72 of additional compounds. The tray 24 is preferably manufactured from plastic through a thermoforming process, vacuum forming process, or injection molding process. Since both the storage tray 24 and the sleeve 50 of the cover 22 are preferably manufactured from plastic, the tray 24 can be heat sealed to the cover 22. In the preferred embodiment, the tray 24 is heat sealed to the cover 22 proximate the bottom segment 34 of the cover 22. The base portions 67 are preferably not heat sealed to the sleeve 50 to enable the individual segments 26 to be folded into the various positions depicted in FIGS. 3 through 6.

In operation, FIGS. 3 through 6 depict some of the positions into which the storage and display apparatus 20 can be transformed. The four positions depicted are only illustrative of the invention, and are not exclusive. With specific reference to FIG. 3, the storage and display apparatus 20 can be folded into a storage position by wrapping the cover 22 around the storage tray 24, and connecting the connection flap 40 to the top 30 with the fastening strips 46. The segments 26 of the cover 22 cooperate with the side walls 42 and 44 of each tray 24 to completely enclose the syringes 70 and bottles 72 stored within the tray 24. More specifically, in the closed configuration of FIG. 3, the cover 22 forms a trapezoid in cross-section with top 30 being parallel to a bottom 34 and bottom extension 36, the first side 32 being non-parallel to the second side 38, and the connection flap 40 being parallel to and in engagement with the top 30. The strips 46 of hook and loop fasteners are hidden from view when the cover 22 is in a closed position.

Figure 4:
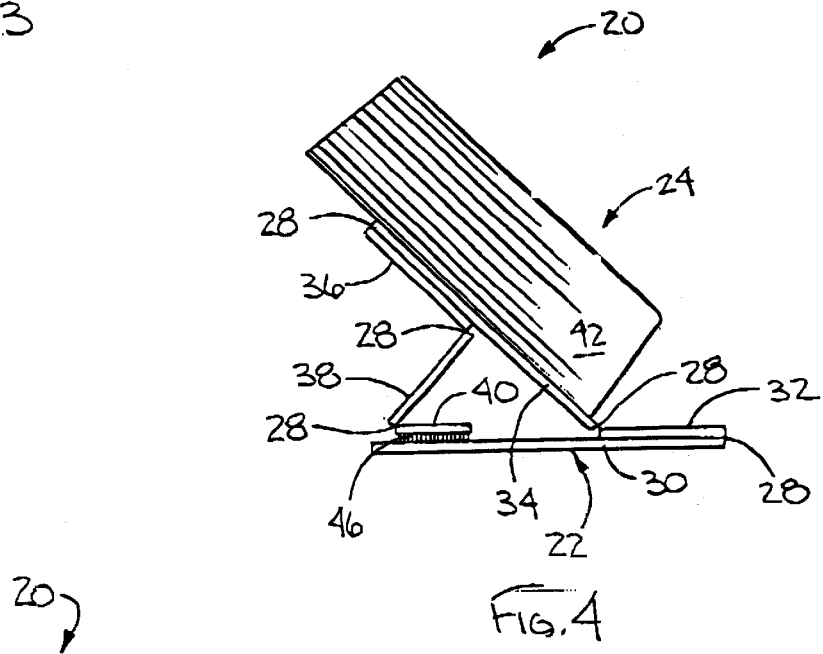
FIG. 4 is a side view of the apparatus shown in FIG. 3 in a first display position.

FIG. 4 depicts the storage and display apparatus 20 after being transformed into a first display or easel position wherein the tray 24 is positioned approximately 45° from horizontal. To reach such a configuration, the connection flap 40 is first detached from the top 30, and then folded approximately 270° with respect to the first side 32 about a hinge 28. In addition, the bottom extension is folded approximately 180° with respect to the bottom 34, with the second side 38 remaining spaced approximately 90° from the bottom extension 36. The connection flap 40 is folded approximately 225° with respect to the second side 38 and reattached to the top 30 using the fastening strips 46. The unique positioning of the fastening strips 46 and reversibility of the flap 40 facilitate this process. The apparatus 20 can then be set upon a suitable work surface, counter top, or the like with the top 30 serving as a horizontal base.

Figure 5:
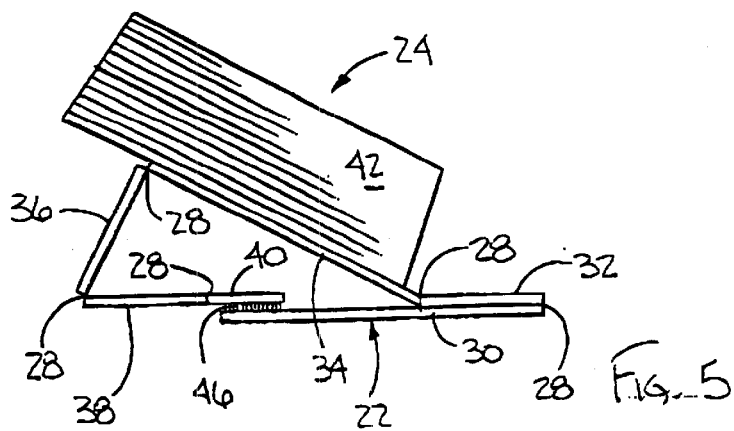
FIG. 5 is a side view of the apparatus shown in FIG. 3 in a second display position.

FIG. 5 depicts a second display position wherein the tray 24 is positioned approximately 30° from horizontal. To reach this position from the position depicted in FIG. 4, the second side 38 is folded parallel to the connection flap 40. In so doing the second side 38 pivots about the hinge 28 and the bottom extension 38 is folded approximately 90° to be orthogonally disposed relative to the bottom 34. A variety of angles can be obtained other than the 45° and 30° angles depicted in FIGS. 4 and 5 by slight movement of the various segments 26. For example, the angle of display will necessarily vary depending on the amount of overlap between the fastener strips 46. Additionally, the apparatus 20 can be opened with the bottom 34 remaining horizontal to thus display tray 24 horizontally as well.

The configurations shown in FIGS. 4 and 5 show that segments 36 and 38 can be completely folded away from the syringes 70 making the handles 71 of the syringes 70 easier to grip and remove from the tray 24. Moreover, the syringes 70 can be more easily returned, and the segments 36 and 38 can be aseptically cleaned without touching or otherwise contaminating the other segments or the other syringes 70.

FIG. 6 depicts an alternative embodiment of the storage and display apparatus 20 in a substantially elevated display position. The substantially elevated display position can be reached from the position depicted in FIG. 4 through the use of a locking sleeve 78. The locking sleeve 78 is preferably made from a substantially rigid material, such as plastic, in the form of a continuous loop. Alternatively, a spring clip (not shown) or other type of mechanical support could be used. The locking sleeve frictionally engages the cover 22 and is slidable between the bottom extension 36 and the second side 38. Accordingly, from the position depicted in FIG. 4, the bottom extension 36 and the second side 38 are folded about the hinge 28 into a parallel configuration. The locking sleeve 78 is then slid over the hinge 28 such that the locking sleeve 78 partially engages the bottom extension 36 and the second side 38. The locking sleeve 78 prohibits pivotal motion about the hinge 28. Moreover, the parallel bottom extension 36 and second side 38 support the bottom 36 and tray 24 at a greater, substantially vertical, angle.

From the foregoing, it will be seen that the storage and display apparatus 20 can be transformed into a plurality of angular displays best suited to the particular user, and to the particular procedure being performed. Moreover, through the use of individual compartments 68 and a cover 22 which can be folded completely away from the top of the tray 24, the syringes 70 and bottles 72 can remain organized, and aseptic, with minimized risk of cross-contamination. When the procedure is completed, the apparatus 20 can be closed for storage, handling, and transportation until subsequent procedures are to be performed.

What is claimed is:

1. A dental equipment and material storage and multi-positional display apparatus comprising:
   a cover having a plurality of hinged segments; and
   a storage tray secured to one of the hinged segments, the storage including a plurality of compartments adapted to store dental equipment and material;
   wherein the cover is foldable from a storage position surrounding the storage tray to a plurality of display positions exposing the storage tray for ready access to the dental equipment and material;
   wherein the storage tray includes a top edge from which portions of the equipment may extend, the cover being completely folded away from the top edge of the storage tray when the cover is in a display position to minimize contact with the cover and thus minimize risk of cross-contamination during use;
   wherein the hinged segments include a top segment, a first side segment, a bottom extension segment, a second side segment and an attachment flap segment that form a trapezoidal enclosure around the storage tray.

2. The apparatus of claim 1 wherein the storage tray is secured to the bottom segment.

3. The apparatus of claim 1 further including an attachment mechanism to secure the attachment flap to the top segment.

4. A dental equipment and material storage and multi-positional display apparatus, comprising:
   a cover having a plurality of hinged segments; and
   a storage tray secured to one of the hinged segments, the storage tray being adapted to store equipment and material, wherein the one of the hinged segments includes a top segment, a first side segment, a bottom segment, a bottom extension segment, a second side segment and an attachment flap segment that form a trapezoidal enclosure around the storage tray;
   a support slidable between the bottom extension segment and the second side segment, the slidable support being positionable on the bottom extension segment and second side segment to lock the bottom extension segment and second side segment into the same plane when the cover is in the display position;
   wherein the cover is foldable from a storage position surrounding the storage tray to a least one display position exposing the storage tray for ready access to the equipment and material.

5. The apparatus of claim 1 wherein the storage tray includes a plurality of compartments to store dental supplies and equipment.

6. A dental equipment and material storage and multi-purpose display apparatus, comprising:
   a cover having a plurality of hinged segments, the cover including a plastic sleeve with a plurality of rigid inserts positioned within the plastic sleeve, a heat seal being provided between each insert, the heat seals defining hinges for the cover,
   a storage tray secured to one of the hinged segments, the storage tray including a plurality of compartments adapted to store dental equipment and material;
   wherein the cover is foldable from a storage position surrounding the storage tray to a plurality of display positions exposing the storage tray for ready access to the dental equipment and material.

7. A dental equipment and material storage device and display easel, comprising:
   a cover having planar segments hinged together, the planar segments including a top segment, a first side segment, a bottom segment, a bottom extension segment, a second side segment, and a connection flap segment, that form a enclosure around the storage device;
   a dental equipment and material storage tray secured to the bottom segment of the cover, the tray including a plurality of compartments adapted to store dental equipment and material, the cover being foldable from a storage position surrounding the tray, to a plurality of display positions exposing the tray; and
   a fastener secured to the top segment, the connection flap segment being secured to the fastener when the cover is in the storage position, the connection flap segment also being secured to the fastener when the cover is in the display position.

8. The storage device and display easel of claim 7 wherein the cover is foldable into multiple display positions to display the equipment and material at a plurality of angles.

9. The storage device and display easel of claim 7 wherein the fastener includes hook and loop fasteners.

10. The storage device and display easel of claim 7 wherein the fastener is a band secured to the top segment, the band forming an opening adapted to frictionally receive the connection flap segment.

11. The storage device and display easel of claim 7 wherein the storage tray includes a plurality of compartments adapted to store dental equipment and supplies.

12. The storage device and display easel of claim 7 wherein the cover includes a plastic sleeve with rigid inserts positioned within the plastic sleeve, a heat seal being provided between adjacent inserts, the heat seals defining hinges for the cover.

13. The storage device and display easel of claim 6 wherein the equipment and material storage tray is plastic and heat sealed to the plastic sleeve.

14. A dental equipment and material storage device and display easel, comprising:
   a tray including a plurality of compartments adapted to store dental equipment and material;
   a housing enclosing the tray compartments to protect the dental equipment and material during storage; and
   means for transforming the housing into an easel for displaying the tray and dental equipment and material at a plurality of angles with respect to a surface on which the storage device and display easel is set.

15. The storage device and display easel of claim 14 wherein the housing includes a plurality of rigid segments and the means for transforming includes a plurality of hinges connecting the rigid segments and a fastener for locking the housing into a plurality of positions.

16. The storage device and display easel of claim 15 wherein the housing further includes a plastic sleeve with the plurality of rigid segments positioned therein, and the plurality of hinges are formed by the heat sealing opposed sides of the plastic sleeve together between adjacent rigid segments.

17. The storage device and display easel of claim 14 wherein the tray includes a plurality of compartments adapted to store the dental equipment and material.

18. The storage device of claim 17 wherein the tray includes a base having the plurality of compartments formed therein, and first and second extended side walls, the first and second extended side walls cooperating with the housing to form a six sided trapezoidal enclosure completely surrounding the dental equipment and material during storage.

* * * * *